(12) United States Patent
Suzuki

(10) Patent No.: US 7,377,646 B2
(45) Date of Patent: May 27, 2008

(54) PERIMETER

(75) Inventor: Naoto Suzuki, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 272 days.

(21) Appl. No.: 11/141,330

(22) Filed: Jun. 1, 2005

(65) Prior Publication Data

US 2005/0280776 A1   Dec. 22, 2005

(30) Foreign Application Priority Data

Jun. 1, 2004   (JP)   ............... 2004-163394

(51) Int. Cl.
*A61B 3/02*   (2006.01)
(52) U.S. Cl. .................................... 351/224
(58) Field of Classification Search ................ 351/224, 351/206, 211; 396/18
See application file for complete search history.

(56) References Cited

U.S. PATENT DOCUMENTS 5,037,194 A    8/1991   Kohayakawa et al.
5,323,194 A    6/1994   Campbell et al.
6,406,437 B1 * 6/2002   Zur et al. .................... 600/558
6,478,424 B1 * 11/2002  Grinvald et al. ............ 351/206
6,705,726 B2   3/2004   Tanassi et al.

* cited by examiner

*Primary Examiner*—Hung Dang
*Assistant Examiner*—Joseph Martinez
(74) *Attorney, Agent, or Firm*—Sughrue Mion, PLLC

(57) ABSTRACT

A perimeter for examining a state of a visual field of a patient's eye includes: a target presenting unit that presents a stimulation target for examination to the eye, a presentation position and a presentation brightness of the target being variable; a first arithmetic unit that obtains a threshold of sensitivity with respect to the presentation brightness at each examination point on a retina corresponding to each presentation position; an input unit that inputs function information at each examination point, the function information at each examination point being objectively obtained by processing a first fundus image of the eye taken before irradiation onto a fundus of the eye and a second fundus image of the eye taken after the irradiation; and a determining unit that determines an initial reference value of the presentation brightness at each presentation position based on the input function information at each examination point.

6 Claims, 3 Drawing Sheets

PERIMETER

BACKGROUND OF THE INVENTION

The present invention relates to a perimeter for examining a state of a visual field of a patient's eye.

When diagnosing disease such as glaucoma, examining (measuring) the state of the visual field (perimetry) is considered to be effective. As an apparatus for examining the state of the visual field (perimeter), such an apparatus is known in which a stimulation target (optotype) for examination is projected on a dome-shaped screen or is displayed on an electronic display panel such as a liquid crystal display to be presented to the patient's eye fixing to a predetermined fixation point while varying a presentation position and a presentation brightness (luminance) of the target, and the minimum brightness at which the patient can visually recognize (perceive) the presented target, that is, the threshold value of sensitivity with respect to the presentation brightness, is examined at each examination point on a retina of the patient's eye corresponding to each presentation position by obtaining whether or not patient can recognize the presented target (see U.S. Pat. No. 6,705,726 (corresponding to JP 2003-235800A)).

However, in this kind of the perimeter, since the presentation brightness of the target is gradually lowered (made darker) from a constant reference value at each of 50 to 100 examination points, it takes a long time for examination, and hence the burden on the patient is significant. Further, if it takes long time for examination and a burden on the patient is significant, reliability of the examination result is reduced.

SUMMARY OF THE INVENTION

In view of such a problem in the related art described above, it is a subject of the present invention to provide a perimeter which can reduce the time required for examination and can obtain an examination result with high accuracy.

In order to solve the aforesaid object, the invention is characterized by having the following arrangement.

(1) A perimeter for examining a state of a visual field of a patient's eye, the perimeter comprising:
  a target presenting unit that presents a stimulation target for examination to the eye, a presentation position and a presentation brightness of the target being variable;
  a first arithmetic unit that obtains a threshold of sensitivity with respect to the presentation brightness at each examination point on a retina of the eye corresponding to each presentation position;
  an input unit that inputs function information at each examination point, the function information at each examination point being objectively obtained by processing a first fundus image of the eye taken before irradiation of visible stimulation light onto a fundus of the eye and a second fundus image of the eye taken after the irradiation of the visible stimulation light; and
  a determining unit that determines an initial reference value of the presentation brightness at each presentation position based on the input function information at each examination point.

(2) The perimeter according to (1), wherein the input unit inputs a change of an absorbance at each examination point as the function information at each examination point.

(3) The perimeter according to (2), wherein the input unit inputs, as the change of the absorbance at each examination point, a value obtained by dividing a brightness of the second fundus image at each examination point by a brightness of the first fundus image at each examination point, or a value obtained by subtracting the brightness of the first fundus image at each examination point from the brightness of the second fundus image at each examination point.

(4) The perimeter according to (1) further comprising:
  a first irradiation optical system that irradiates the visible stimulation light onto the fundus;
  a second irradiation optical system that irradiates illumination light different from the visible stimulation light onto the fundus;
  an imaging optical system that includes an objective lens and an imaging element and images, as the first and second fundus images, a fundus image by the illumination light reflected from the fundus; and
  a second arithmetic unit that obtains the function information at each examination point by processing the first and second images imaged by the imaging element,
  wherein the input unit inputs the function information at each examination point obtained by the second arithmetic unit.

(5) The perimeter according to (4), wherein
  the first irradiation optical system is an optical system that irradiates visible illumination light for a fundus visible photographing onto the fundus, and
  the second irradiation optical system is an optical system that irradiates infrared illumination light for a fundus infrared observation onto the fundus.

(6) The perimeter according to (4), wherein the target presenting unit comprises a target presenting optical system that presents the target to the eye through the objective lens.

DETAILED DESCRIPTION OF PREFERRED EMBODIMENTS

Figure 1:
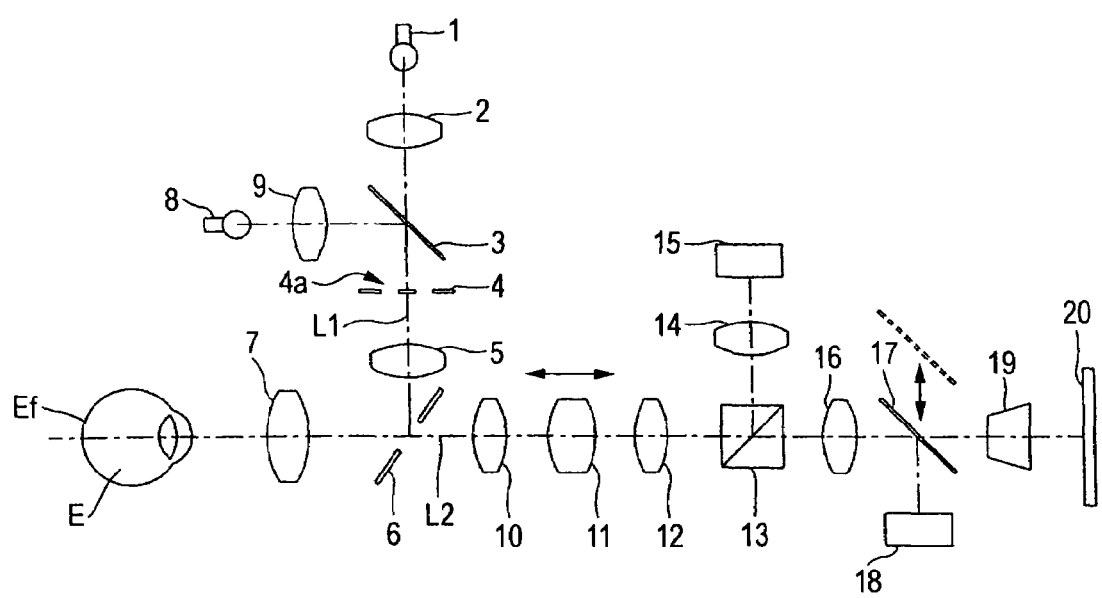
FIG. 1 is a drawing showing an optical system of a perimeter according to the present embodiment.
Figure 2:
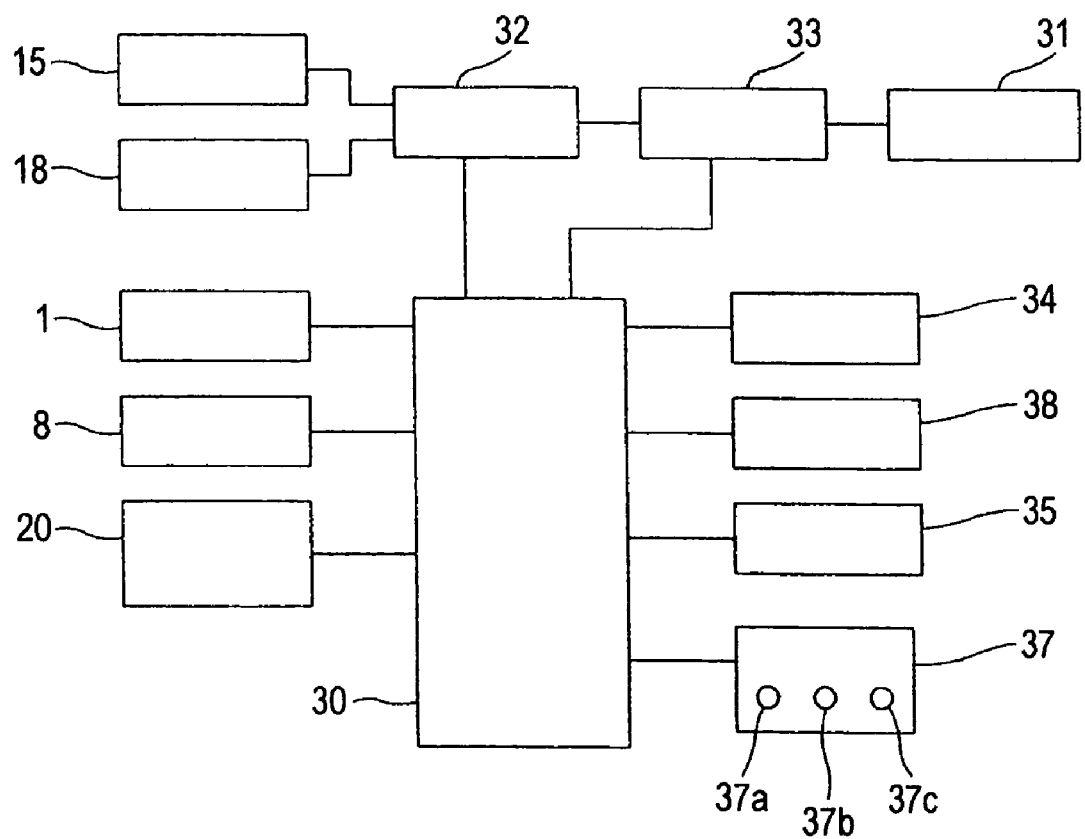
FIG. 2 is a block diagram showing a control system of the perimeter according to the present embodiment.

Referring now to drawings, an embodiment of the present invention will be described. FIG. 1 is a schematic structural diagram showing an optical system of a perimeter according to this embodiment. FIG. 2 is a schematic block diagram of a control system of the perimeter. This perimeter has a function of fundus photography (a fundus camera) and a function of measuring the retina function (sensitiveness of a retina, etc) objectively in addition to a function of examining a state of a visual field subjectively (perimetry).

Symbol "E" shows a patient's eye, i.e. an eye to be examined. Visible to infrared light emitted from an observation-purpose illumination light source 1 such as a halogen lamp is converted into infrared illumination light by an infrared transmission filter (not shown) and illuminates a slit plate 4 having a ring slit 4a via a condenser lens 2 and a dichroic mirror (cold mirror) 3. The light (ring slit light)

which has passed through the ring slit 4a forms an intermediate image in the vicinity of an aperture (opening) of a hole mirror 6 via a relay lens 5, and also, is reflected by a peripheral plane of the mirror 6 around the aperture. The light reflected by the mirror 6 is once focused in the vicinity of a pupil of the eye E by an objective lens 7, and thereafter, is diffused so as to illuminate a fundus "Ef" of the eye E uniformly. The mirror 3 has such a wavelength selection characteristic as to reflect visible light thereby, while passing infrared light therethrough. On the other hand, visible illumination light emitted from a photographing-purpose (imaging-purpose) illumination light source 8 such as a xenon flash lamp is traveled via another condenser lens 9, reflected by the mirror 3, and traveled via the optical elements from the slit plate 4 to the lens 7 to illuminate the fundus Ef. An illumination optical system (namely, both observation-purpose illumination optical system and photographing-purpose (imaging-purpose) illumination optical system) is formed by this construction. In addition, instead of the light source 1 and the infrared transmission filter, an infrared illumination light source may be alternatively employed. The optical system from the light source 8 to the lens 7 also serves as an optical system for irradiating visible stimulation light onto the fundus Ef when the retina function is measured.

The infrared reflection light reflected from the fundus Ef is traveled through the lens 7, the aperture of the mirror 6, lenses 10, 11, 12, is reflected by a dichroic mirror 13, traveled through a lens 14 and focused onto a light receiving plane of an observation-purpose camera 15 having a sensitivity in an infrared region. The mirror 13 has such a wavelength selection characteristic as to reflect infrared light thereby, while passing visible light therethrough. The aperture of the mirror 6 is at an optical conjugate position with respect to the pupil of the eye E, and constitutes a diaphragm. The lens 11 is movable in an optical axis direction to put the fundus Ef and the light receiving plane of the camera 15 into an optical conjugate positional relationship. An infrared imaging optical system which also serves as an observation optical system is constructed in this fashion.

On the other hand, visible reflection light reflected from the fundus Ef is traveled via optical elements from the lens 7 to the lens 12 similarly to the infrared reflection light, traveled via the mirror 13 and a lens 16, reflected by a reflection mirror 17 and focused onto a light receiving plane of a photographing-purpose (imaging-purpose) camera 18 having a sensitivity in a visible region. The light receiving plane of the camera 18 and the light receiving plane of the camera 15 are positioned to have an optical conjugate positional relationship. A photographing (visible imaging) optical system is constructed in this fashion.

The optical axis L1 of the illumination optical system (lenses 2, 5, 9) and an optical axis L2 of the observation optical system and the photographing optical system (lenses 10, 11, 12, 14, 16) are coaxial with an optical axis of the lens 7.

The target presenting optical system for examining the state of the view field (perimetry) is arranged by commonly using the optical elements from the lens 7 to the lens 16 of the photographing optical system, and by employing a reducing lens 19 and a liquid crystal display (LCD) 20 for presenting a stimulation target (optotype) for examination. The lens 19 is employed so as to focus an entire image of the target presenting region of the LCD 20 onto the eye E. When the perimetry is carried out (when the target is presented), the mirror 17 is moved out of the optical path. The target presented on the LCD 20 is projected via the optical elements from the lens 19 to the objective lens 7 onto the fundus Ef. An eye fixation target (eye fixation point) having a cross shape is formed on a center (on the optical axis "L2") of the LCD 20. As to the stimulation target, a presentation position thereof, a presentation brightness (luminance) thereof, a presentation size thereof, and others can be varied.

The light source 1, the light source 8, the LCD 20, an image processing unit 32, an image switching unit 33, memories 34, 38, a response button 35, a control portion 37 equipped with a various button, switch and keys, and the like are connected to an arithmetic control unit 30 for driving and controlling an entire system of the apparatus (perimeter). The button 35 is pushed (manipulated) when the patient can visually recognize (perceive) a presented target during perimetry. The control portion 37 is equipped with a photographing button 37a, a mode switching button 37b for switching a perimetry mode, a retina function measurement mode and a fundus photographing mode, and a start button 37c for the measurement of the retina function and the perimetry, and so on.

The image processing unit 32 performs an image processing operation with respect to images obtained by the camera 15 and the camera 18. The image switching unit 33 switches an observation image in the form of time-varying image obtained by the camera 15 and a photograph image in the form of a still image obtained by the camera 18 so that any one of the observation image and the photograph image is displayed on the monitor 31. The memory 34 stores therein the images obtained by the cameras 15, 18 and response information (subjective information) obtained from the patient during perimetry. The arithmetic control unit 30 performs arithmetic processing in the measurement the retina function and arithmetic processing the perimetry.

The operation of the perimeter having the construction as described above will be described. Hereinafter, the case in which the retina function measurement mode is firstly carried out and the perimetry mode will be described.

In the case of the retina function measurement mode, the light source 1 is turned on, and an image of the fundus Ef illuminated by the infrared light is picked up by the camera 15. An examiner moves the apparatus with respect to the eye E by operating a joystick or the like while observing the infrared fundus image displayed on the monitor 31 to align the apparatus with respect to the eye E. The examiner performs focusing with respect to the fundus Ef by bringing the infrared fundus image into focus by moving the lens 11 the optical axis direction. In the case of the retina function measurement, the mirror 17 is moved out of the optical path and the eye fixation target is formed at the center (on the optical axis L2) of the LCD 20.

Figure 4:
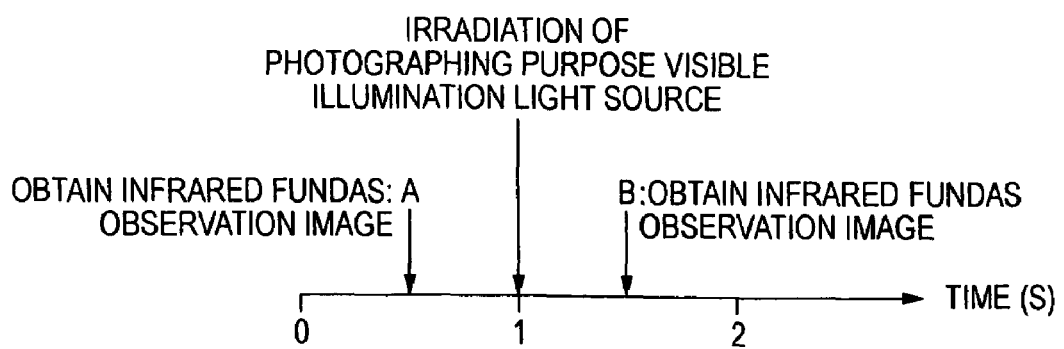
FIG. 4 is a drawing explaining the procedure of obtaining an infrared fundus observation image.

When alignment and focusing are achieved, the examiner pushes the button 37c, and carries out the retina function measurement. In the retina function measurement, as shown in FIG. 4, at least two images of an infrared fundus observation image A before light emission from the light source 8 and an infrared fundus observation image B after the light emission. In response to a trigger signal from the button 37c, the arithmetic control unit 30 picks up the fundus image illuminated by the infrared light by the camera 15 and stores the fundus image A in the memory 34. After obtaining the fundus image A, the light source 8 emits light after a predetermined time (after 0.5 second) to irradiate visible stimulation light onto the eye E. At this time, the arithmetic control unit 30 performs the visible photographing of the fundus Ef simultaneously. By inserting the mirror 17 into the optical path synchronously with the light emission from the light source 8, the visible reflecting light from the fungus Ef is guided to the camera 18 and the visible fundus photograph image is obtained. This fundus image is stored in the memory 34. When visible photographing is completed, the arithmetic control unit 30 causes the mirror 17 to move out of the optical path again. Subsequently, the fundus image illuminated by the infrared light again is picked up by the camera 15 after a predetermined time from the light emission of the light source 8 (after 0.5 seconds to 3 seconds, preferably after 0.5 seconds which is a short time from the light emission), and the fundus image B is stored in the memory 34.

When the fundus images A and B are obtained, the arithmetic control unit 30 obtains endogenous signals showing information on the retina function by comparing a brightness of the fundus image A before irradiation of the visible stimulation light and a brightness of the fundus image B after the irradiation of the visible stimulation light. Measurement of the retina function can be achieved by the technology proposed in Development of a new examination method for a retina function by an optical measuring method" by Kakuta, et. al, Journal of Japanese Ophthalmological Society, an abstract of lectures in the 107th General Assembly of Japanese Ophthalmological Society, issued on Mar. 15, 2003, P. 299). That is, when a retina cell is stimulated by visible light (irradiating the visible stimulation light to a retina), the activity of nerve cells occurs and consumption of oxygen and change of the cellular organization occur. Then, when infrared light is irradiated to the retina before and after the irradiation of the visible stimulation light, the strength of the infrared reflection light changes (absorbance on the retina changes). Therefore, by comparing the brightness between two obtained infrared fundus images before and after irradiation of the visible stimulation light, the endogenous signals indicating information on the retina function are obtained. In an example of the present embodiment, a value (Pb/Pa) obtained by dividing a brightness Pb of the fundus image B by a brightness Pa of the fundus image A is obtained as an endogenous signal. The endogenous signals are obtained at 76 points on the fundus Ef shown in, for example, FIG. 3 corresponding to the respective examination points for perimetry, and are stored in the memory 34 (information on the retina function is entered). As regards comparison between the fundus images A, B, it is preferable to compensate the positional displacement of these images into alignment by a method of matching a characteristic point common to the both images.

After completion of the retina function measurement, the mode is switched to the perimetry mode by the button 37*b*. When switched to the perimetry mode, the arithmetic control unit 30 determines the initial reference value of the presentation brightness of the target to be presented by the LCD 20 (brightness when examination is started) based on the endogenous signals stored in the memory 34 for each of 76 examination points.

At the points where the activity of the retina nerve cells is not vigorous, the value of the endogenous signal becomes close to 1 (difference in brightness between the fundus image A and the fundus image B is small). On the other hand, at the points where the activity of nerve cells is vigorous, the endogenous signal shows a low value. Therefore, at the examination points where the value of the endogenous signal is close to 1, the initial reference value of the presentation brightness of the target is set to the highest brightness (0 db). At the examination points where the endogenous signals S1 are lower than a predetermined threshold, the initial reference value of the presentation brightness is set to a rather lower brightness (for example, 20 db). Furthermore, it is also possible to set the brightness, not only in two stages, but also to three stages, four stages . . . and so on, so as to vary stepwise depending on the level of the endogenous signals. The relation between the initial reference value of the presentation brightness and the endogenous signals is stored in a memory 38 as the table in advance, and the initial reference value of the presentation brightness is determined at each of 76 examination points based on this table.

In the perimetry, the arithmetic control unit 30 starts measurement with starting the examination target at each examination point from the initial reference value determined in the manner described above. Upon reception of the response (entry of response signal) of the button 35 from the patient, the presentation brightness of the target at the corresponding examination point is lowered (made darker) in sequence by a predetermined brightness (4 db). On the other hand, when no response from the patient is received, the brightness is increased by the predetermined brightness (made brighter) on the contrary. Before and after occurrence of response of recognition, the brightness is increased or reduced by the amount corresponding to 1 db, and the darkest brightness which the patient could recognize finally is set as the threshold at the corresponding examination point. The same procedure is carried out at 76 examination points. By defining the initial reference value of the presentation brightness from which the brightness is started at each examination points based on information obtained through the retina function measurement in advance, a time required for examination can be significantly reduced in comparison with the case of employing a constant brightness (for example, 0 db) all the time. In other words, by starting from the initial reference value of the presentation brightness at low brightness (brightness close to 40 db) at the examination points where the sensitiveness of retina is relatively high, the time required for measurement is significantly reduced.

Figure 3:
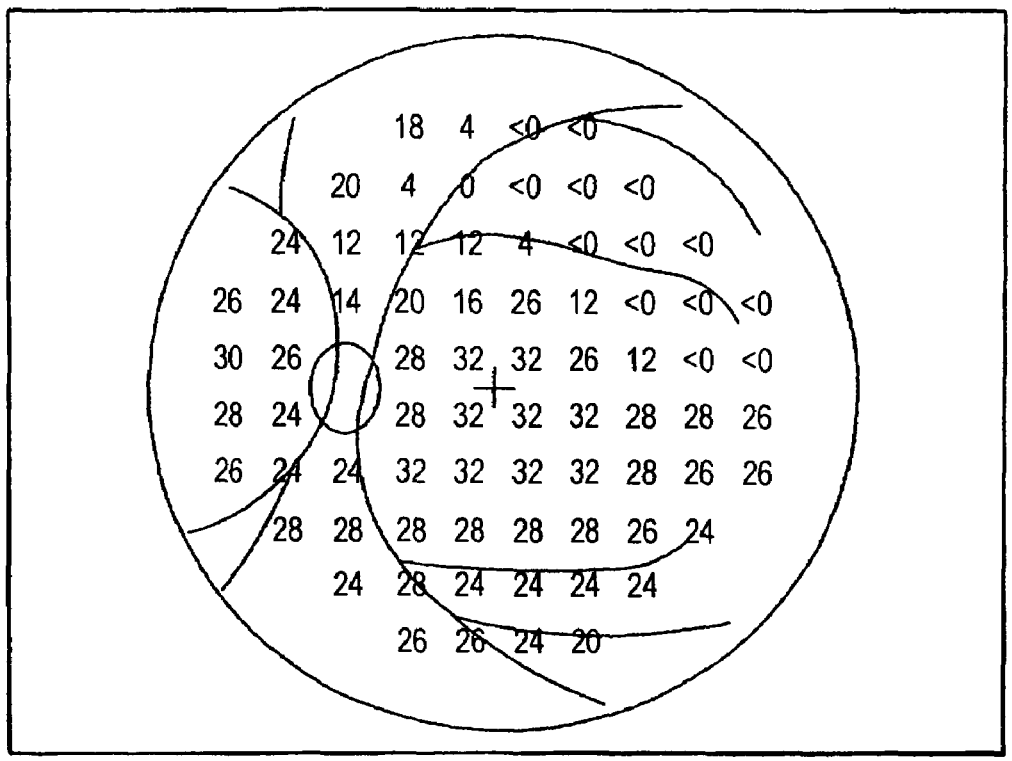
FIG. 3 is a drawing showing a fundus image and thresholds of brightness displayed on a monitor.

When the measurement of the visual field is terminated for every 76 examination points on the fundus Ef, as shown in FIG. 3, the result of measurement in which all the thresholds of 76 points are superimposed on the fundus image taken by the camera 18 stored in the memory 34 is displayed on the monitor 31.

The embodiment described above can be changed in various manners. For example, the endogenous signals may be a value (Pb-Pa) obtained by subtracting a brightness Pa of the fundus image A from a brightness Pb of the fundus image B.

The correspondence relation of the reference value of the presentation brightness with respect to the endogenous signals can be determined continuously in fines. In addition, it is also conceivable to determine the initial reference value of the presentation brightness by obtaining sample data of the values of the endogenous signals as a result of execution of the retina function measurement and the threshold (brightness) as a result of execution of the perimetry according to the threshold examination method for eyes of a number of different patients in advance and finding an approximated curve of the relation therebetween by statistical work. In this case, the brightness which is increased from the brightness of the approximated curve by a predetermined amount with respect to the endogenous signals is determined as the initial reference value of the presentation brightness.

The common utilization of the optical systems can be achieved by integrating the optical system for measuring the retina function and the arithmetic processing system into the perimeter, whereby an apparatus advantageous in space saving or economically is achieved. However, as regards the parts for measuring the retina function may be a separate apparatus. In this case, means for inputting information on retina function (value of the endogenous signal) measured into the perimeter by data transmission or the like. With respect to the information on the retina function, data corresponding to the respective examination points for the perimetry may be extracted to input only the extracted data in the perimeter in advance, or data corresponding to the respective examination points may be extracted by the perimeter for use.

What is claimed is:

1. A perimeter for examining a state of a visual field of a patient's eye, the perimeter comprising:
    a target presenting unit that presents a stimulation target for examination to the eye, a presentation position and a presentation brightness of the target being variable;
    a response unit that provides a response indicating that the patient recognizes the target presented by the target presenting unit;
    a first arithmetic unit that obtains a threshold of sensitivity at each examination point on a retina of the eye corresponding to each presentation position based on the response provided by the response unit and the presentation brightness at each examination point;
    an input unit that inputs function information at each examination point, the function information at each examination point being objectively obtained by processing a first fundus image of the eye taken before irradiation of visible stimulation light onto a fundus of the eye and a second fundus image of the eye taken after the irradiation of the visible stimulation light; and
    a determining unit that determines an initial reference value of the presentation brightness at each presentation position based on the input function information at each examination point.

2. The perimeter according to claim 1, wherein the input unit inputs a change of an absorbance at each examination point as the function information at each examination point.

3. The perimeter according to claim 2, wherein the input unit inputs, as the change of the absorbance at each examination point, a value obtained by dividing a brightness of the second fundus image at each examination point by a brightness of the first fundus image at each examination point, or a value obtained by subtracting the brightness of the first fundus image at each examination point from the brightness of the second fundus image at each examination point.

4. The perimeter according to claim 1 further comprising:
    a first irradiation optical system that irradiates the visible stimulation light onto the fundus;
    a second irradiation optical system that irradiates illumination light different from the visible stimulation light onto the fundus;
    an imaging optical system that includes an objective lens and an imaging element and images, as the first and second fundus images, a fundus image by the illumination light reflected from the fundus; and
    a second arithmetic unit that obtains the function information at each examination point by processing the first and second images imaged by the imaging element,
    wherein the input unit inputs the function information at each examination point obtained by the second arithmetic unit.

5. The perimeter according to claim 4, wherein
    the first irradiation optical system is an optical system that irradiates visible illumination light for a fundus visible photographing onto the fundus, and
    the second irradiation optical system is an optical system that irradiates infrared illumination light for a fundus infrared observation onto the fundus.

6. The perimeter according to claim 4, wherein the target presenting unit comprises a target presenting optical system that presents the target to the eye through the objective lens.

* * * * *